US012402836B2

(12) United States Patent
Labbe et al.

(10) Patent No.: US 12,402,836 B2
(45) Date of Patent: Sep. 2, 2025

(54) METHOD AND SYSTEM FOR CALIBRATING SENSING CIRCUITRY OF AN IMPLANTED MEDICAL DEVICE

(71) Applicant: Pacesetter, Inc., Sylmar, CA (US)

(72) Inventors: Eric Labbe, Sunnyvale, CA (US); Dean Andersen, Santa Clara, CA (US); Shuo Li, Burbank, CA (US)

(73) Assignee: Pacesetter, Inc., Sylmar (CA)

( * ) Notice: Subject to any disclaimer, the term of this patent is extended or adjusted under 35 U.S.C. 154(b) by 681 days.

(21) Appl. No.: 17/810,923

(22) Filed: Jul. 6, 2022

(65) Prior Publication Data

US 2023/0083815 A1   Mar. 16, 2023

Related U.S. Application Data

(60) Provisional application No. 63/261,237, filed on Sep. 15, 2021.

(51) Int. Cl.
*A61B 5/00*   (2006.01)

(52) U.S. Cl.
CPC .................................. *A61B 5/686* (2013.01)

(58) Field of Classification Search
CPC ........ A61B 5/686; A61B 5/053; A61N 1/3756
See application file for complete search history.

(56) References Cited

U.S. PATENT DOCUMENTS

| 2007/0088223 | A1* | 4/2007 | Mann | A61B 5/349 |
| | | | | 600/485 |
| 2014/0355655 | A1* | 12/2014 | Chakraborty | H04B 1/40 |
| | | | | 375/219 |
| 2021/0030295 | A1* | 2/2021 | Shute | A61B 5/1118 |

* cited by examiner

*Primary Examiner* — Jennifer Bahls
(74) *Attorney, Agent, or Firm* — Dean D. Small; The Small Patent Law Group, LLC (57) ABSTRACT

A system is provided that includes electrodes configured to be implanted in a body, and a pulse generator (PG) circuitry to deliver a stimulus to one or more of the electrodes. The system also includes sensing circuitry configured to define a sensing channel between one or more of the electrodes to sense signals indicative of a physiologic activity of interest, and the sensing circuitry further configured to collect a calibration signal over the sensing channel. The sensing circuitry and PG circuitry are housed within an implantable medical device (IMD). The system also includes one or more processors configured to determine a signal characteristic of interest (COI) of the calibration signal. The one or more processors are also configured to compare a signal COI of the stimulus to the signal COI of the calibration signal, and adjust a parameter of the sensing circuitry or PG circuitry based on the comparison.

20 Claims, 5 Drawing Sheets

METHOD AND SYSTEM FOR CALIBRATING SENSING CIRCUITRY OF AN IMPLANTED MEDICAL DEVICE

CROSS-REFERENCE TO RELATED APPLICATIONS

This application claims priority to U.S. Provisional Patent Application No. 63/261,237, filed Sep. 15, 2021 and titled Method and System for Calibrating Sensing Circuitry of an Implanted Medical Device. The subject matter of the provisional application is expressly incorporated herein by reference in its entirety.

BACKGROUND

Embodiments of the present disclosure generally relate to methods and systems for calibrating a therapy circuitry of an implanted medical device.

Intracardiac electrogram activity is constantly recorded by the sensing circuitry of an implantable medical device (IMD). Sensed events are converted from analog to digital signals and are used by IMD logic to determine normal sinus rhythm versus arrhythmia. Such characteristics as R-wave interval timing are used to determine the need for pacing pulses. How long these cardiac events can be detected and/or accurately reported is defined by the sensitivity or gain of the sensing channel.

The gain of the sensing channel can be adjusted in the analog amplifiers or in the digital domain. The gain adjustment can be in very small steps such as in steps of a few µV's. With this fine of resolution, the sensitivity of a device can be tuned to a very high degree of accuracy. However, the sensing channel gain must be trimmed or calibrated for each device because of natural variation in each integrated circuit (IC) and can vary from part to part due to the tolerances of components used in the sensing circuit.

Currently, calibration of the sensing channel is performed during manufacturing. A small stimulus from external test equipment of known amplitude is generated at the input of the sensing channel to emulate the amplitude of a heart signal. The response is analyzed at the output of the sensing channel such that the overall sensing channel gain is extracted and stored in non-volatile memory. However, the small input stimulus is prone to be corrupted by external noise sources which limits how the sensitivity can be optimized for each part. In addition, the associated test time to perform this calibration is fairly long. In addition, the calibration is often performed at just the integrated circuit test stage. Consequently, there is no way to account for external components in the sensing circuitry that are used in the final product that are not a part of the test stage. Consequently, any losses associated with the components external to the IC used at the time of implant are not considered, leading to improper calibration.

SUMMARY

In accordance with an embodiment, a system, is provided that includes electrodes configured to be implanted in a body, and a pulse generator (PG) circuitry to deliver a stimulus to one or more of the electrodes. The stimulus includes a signal characteristic of interest (COI). The system also includes sensing circuitry configured to define a sensing channel between one or more of the electrodes to sense signals indicative of a physiologic activity of interest, and the sensing circuitry further configured to collect a calibration signal over the sensing channel. The sensing circuitry and PG circuitry are housed within an implantable medical device (IMD). The system also includes one or more processors, and a memory coupled to the one or more processors. The memory is configured to store program instructions that are executable by the one or more processors to determine a signal COI of the calibration signal. The one or more processors are also configured to compare the signal COI of the stimulus to the signal COI of the calibration signal, and adjust a parameter of the sensing circuitry or PG circuitry based on the comparison.

Optionally, the one or more processors are further configured to adjust, as the parameter, at least one of a gain, or a sensitivity correction factor in an analog/digital converter (ADC), of the sensing circuitry. In one aspect, to adjust the parameter of the sensing circuitry or PG circuitry based on the comparison, the one or more processors are further configured to convert, with analog to digital converter (ADC) of the sensing circuitry, an analog output of an amplifier to a digital value. The one or more processors are also configured to obtain a sensitivity correction factor to vary the digital value. In another aspect, the sensing circuitry includes a first header node and a second header node coupled to a first analog to digital converter, and a third header node coupled to a second analog to digital converter. In one example, the PG circuitry includes a first amplifier electrically coupled to a first control element, and second amplifier electrically coupled to a second control element.

Optionally, the system also includes sensing conductors, within the sensing channel, extending between the sensing circuitry and corresponding header nodes internal to a housing of the IMD, and PG conductors extending between the PG circuitry and the header nodes internal to the housing of the IMD. Alternatively, the system also includes switches configured to connect and disconnect the PG circuit to the header nodes. In another aspect, the stimulus has an energy level that avoids capture. In one example, the sensing channel utilizes a first electrode and a second electrode from the electrodes and the stimulus is delivered to the first electrode and a third electrode from the electrodes. In another example, the sensing channel includes an atrial sensing channel between the first electrode and the third electrode and a ventricular sensing channel between the second electrode and the third electrode. In yet another example, the PG circuitry is configured to deliver an atrial calibration stimulus to the first electrode and third electrode and to deliver a ventricular calibration stimulus to the second electrode and third electrode. Optionally, the one or more processors are also configured to select adjustment of the parameter in one of the atrial sensing channel, or the ventricular sensing channel to update calibration. In one embodiment, the stimulus is one of a therapy stimulus or a calibration stimulus. Alternatively, the therapy stimulus provides a greater energy level than an energy level of the calibration stimulus.

In accordance with an embodiment, a method is provided for calibrating sensing circuitry of an implantable medical device. The method includes delivering, with pulse generator (PG) circuitry, a stimulus to one or more electrodes configured to be implanted in a body, the stimulus having a signal characteristic of interest (COI). The method also includes sensing, with the sensing circuitry, signals indicative of physiologic activity of interest, wherein the sensing circuitry and PG circuitry are housed within the implantable medical device (IMD). The method also includes collecting, with the sensing circuitry, a calibration signal over a sensing channel, and determining a signal COI of the calibration signal. The method also includes comparing the signal COI of the stimulus to the signal COI of the calibration signal, and adjusting a parameter of the sensing circuitry or PG circuitry based on the comparison.

Optionally, adjusting the parameter of the sensing circuitry or PG circuitry includes at least one of adjusting a gain of the PG circuitry, or adjusting a sensitivity correction factor in an analog to digital converter (ADC) of the sensing circuitry. In one aspect, adjusting the parameter of the sensing circuitry or PG circuitry includes converting, with an analog to digital converter (ADC) of the sensing circuitry, an analog output of an amplifier to a digital value, and obtaining a sensitivity correction factor to vary the digital value. In another aspect, the method also includes delivering an atrial calibration stimulus to a first electrode and a third electrode of the sensing circuitry to generate an atrial calibration signal, and delivering a ventricular calibration stimulus to a second electrode and the third electrode to generate a ventricular calibration signal. In one example, the method also includes actuating, with an electrode controller, a first switch to deliver the atrial calibration stimulus to the first electrode and the third electrode, and a second switch to deliver the ventricular calibration signal to the second electrode and the third electrode. In another example, the method also includes selecting adjustment of the parameter in one of an atrial sensing channel, or a ventricular sensing channel, and calibrating the sensing circuitry based on the adjustment selected.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Provided is a system, method, and implementation that eliminates the need to determine the gain/sensitivity of a sensing channel by using an external stimulus. The method accounts for all components that effect gain/sensitivity to a for a higher degree of accuracy by providing a calibration signal through the pacing electrodes that provide a stimulus treatment signal, or therapy signal. The calibration signal avoids capture (e.g. is not able to stimulate treatment); however, does result in the sensing circuitry being utilized in a manner that can be used for calibration. The stimulus used is able to avoid capture because the stimulus is variable in amplitude and pulse width such that even if used in an implant, the energy level applied would safely be under the energy level needed to stimulate. To this end, the system utilizes the external and internal components that impact the sensitivity by generating the input stimulus at the electrodes, therefore the whole sensing channel path is included. Moreover, this method and implementation can be fully automated to allow more coverage (such as testing all gains or filter characteristics) of sensing channels. Finally, such method and calibration circuitry may be used even after implanting of an IMD to calibrate a sensing channel in real-time by determining the actual gain/sensitivity of the sensing circuitry.

Terms

The terms "cardiac activity signal", "cardiac activity signals", "CA signal" and "CA signals" (collectively "CA signals") are used interchangeably throughout to refer to measured signals indicative of cardiac activity by a region or chamber of interest. Cardiac activity in indicative of physiological activity of interest of a patient. For example, the CA signals may be indicative of impedance, electrical or mechanical activity by one or more chambers (e.g., left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes EGM signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The term "sensing vector" shall refer to a path extending between two or more physical, actual electrodes that operate as sensing sites.

The term "capture" as used herein refers to a stimulus that generates a pulse or signal that has an energy level that causes the heart, tissue, nervous system, etc. to react, or pace. In one example, when a therapy signal is generated, the stimulus captures the heart because the energy level of the therapy signal paces the heart. However, when a stimulus generates a calibration signal, or pulse, the energy level of the calibration signal is weaker than the energy level of the therapy signal resulting in no reaction, pacing, or the like by the heart, tissue, nervous system, etc. In this manner, the stimulus has an energy level that avoids capture.

The term "measured impedance" shall refer to intracardiac and/or intrathoracic impedance measurements directly measured from a combination of electrodes positioned within the heart, proximate to the heart and/or within the chest wall.

The term "sensitivity level", as used herein, refers to a threshold that an input CA signal must exceed for an implantable device to identify a CA signal feature of interest (e.g., an R-wave). As one non-limiting example, software may be implemented using a programmed sensitivity level to declare an R-wave to be detected when the input CA signal exceeds the current programmed sensitivity level. In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with amplitude of 0.14 mV will not be detected as an R-wave. Embodiments herein determine an adaptive sensitivity limit and sensitivity profile for the sensitivity level. To this end, a sensitivity correction factor can be a parameter that is adjusted for calibration of sensing circuitry of the IMD.

The terms "normal" and "sinus" are used to refer to events, features, and characteristics of, or appropriate to, a heart's healthy or normal functioning.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "real-time" refers to a time frame contemporaneous with an occurrence such as calibrating therapy circuitry. For example, a real-time process or operation would occur during or immediately after (e.g., within seconds after) a determination is made that calibration of either pulse generating circuitry or sensing circuitry is required. For example, the term "real-time" may refer to a time period substantially contemporaneous with a determination that adjustment of a parameter of pulse generating circuitry or sensing circuitry is required.

The term "subcutaneous" shall mean below the skin, but not intravenous. For example, a subcutaneous electrode/lead does not include an electrode/lead located in a chamber of the heart, in a vein on the heart, or in the lateral or posterior branches of the coronary sinus.

Figure 1:
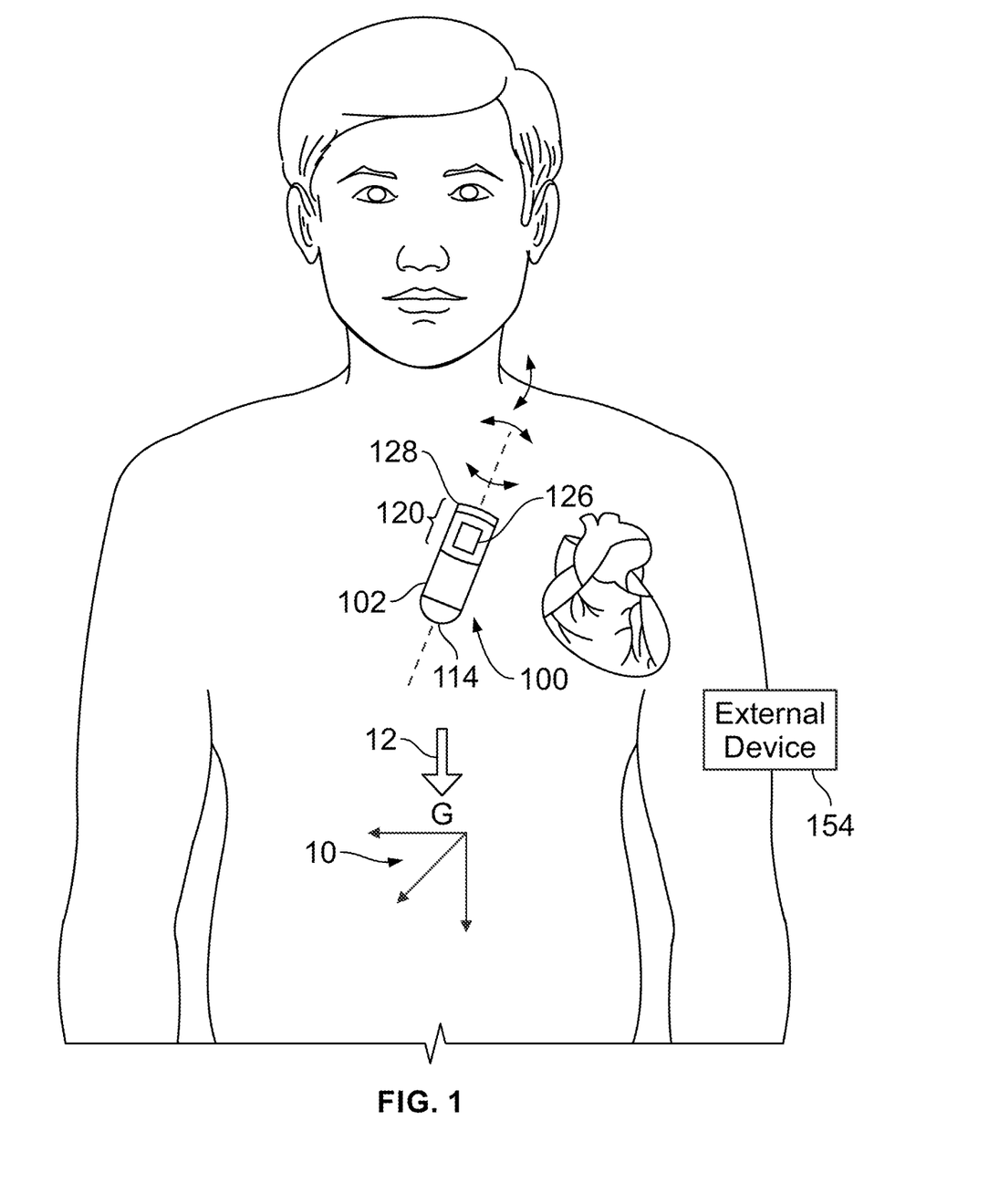
FIG. 1 illustrates a graphical representation of a heart with an implantable medical device (IMD) in accordance with embodiments herein.

FIG. 1 illustrates an implantable medical device (IMD) 100 intended for subcutaneous implantation at a site near the heart. The IMD 100 includes a pair of spaced-apart electrodes 114, 126 positioned with respect to a housing 102. The electrodes 114, 126 provide for detection of far field electrogram signals. In example embodiments the electrodes can be ring electrodes, coil electrodes, tip electrodes, Aring electrodes, Vring electrodes, case electrodes, a combination thereof, or the like.

Numerous configurations of electrode arrangements are possible. For example, the electrode 114 may be located on a distal end of the IMD 100, while the electrode 126 is located on a proximal side of the IMD 100. Additionally or alternatively, electrodes 126 may be located on opposite sides of the IMD 100, opposite ends or elsewhere. The distal electrode 114 may be formed as part of the housing 102, for example, by coating all but a portion of the housing with a nonconductive material such that the uncoated portion forms the electrode 114. In one example, the housing is a case, and at least one of the electrodes is a case electrode. In an embodiment when the electrode 114 is a case electrode, the electrode 126 may be electrically isolated from the case electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.).

The housing 102 includes various other components such as: sensing circuitry for collecting signals over a sensing channel from the electrodes, a microprocessor for analyzing the far field CA signals, including assessing the presence of R-waves in cardiac beats occurring while the IMD is in different IMD locations relative to gravitational force, a loop memory for temporary storage of CA data, a device memory for long-term storage of CA data, sensors for detecting patient activity, including an accelerometer for detecting acceleration signatures indicative of heart sound, and a battery for powering components.

In at least some embodiments, the IMD 100 is configured to be placed subcutaneously utilizing a minimally invasive approach. Subcutaneous electrodes are provided on the housing 102 to simplify the implant procedure and eliminate a need for a transvenous lead system. The electrodes may be located on opposite sides of the device and designed to provide robust episode detection through consistent contact at a sensor-tissue interface. The IMD 100 may be configured to be activated by the patient or automatically activated, in connection with recording subcutaneous ECG signals.

The IMD 100 senses far field, subcutaneous CA signals, processes the CA signals to detect arrhythmias and if an arrhythmia is detected, automatically records the CA signals in memory for subsequent transmission to an external device 154. In addition, when a calibration signal is utilized, signal characteristics of interest (COI) of the calibration signal, signal COI of a stimulus that generates the calibration signal, etc. may also be transmitted to the external device 154 for review and analysis. In example embodiments, a signal COI can be an energy level, amplitude, pulse width, frequency, or the like.

The IMD 100 is implanted in a position and orientation such that, when the patient stands, the IMD 100 is located at a reference position and orientation with respect to a global coordinate system 10 that is defined relative to a gravitational direction 12. For example, the gravitational direction 12 is along the Z-axis while the X-axis is between the left and right arms.

The IMD 100 can also include one or more sensors to collect acceleration signatures that are indicative of heart sounds produced at different points in a cardiac cycle. In one example, an accelerometer is utilized for collecting the acceleration signatures.

Figure 2:
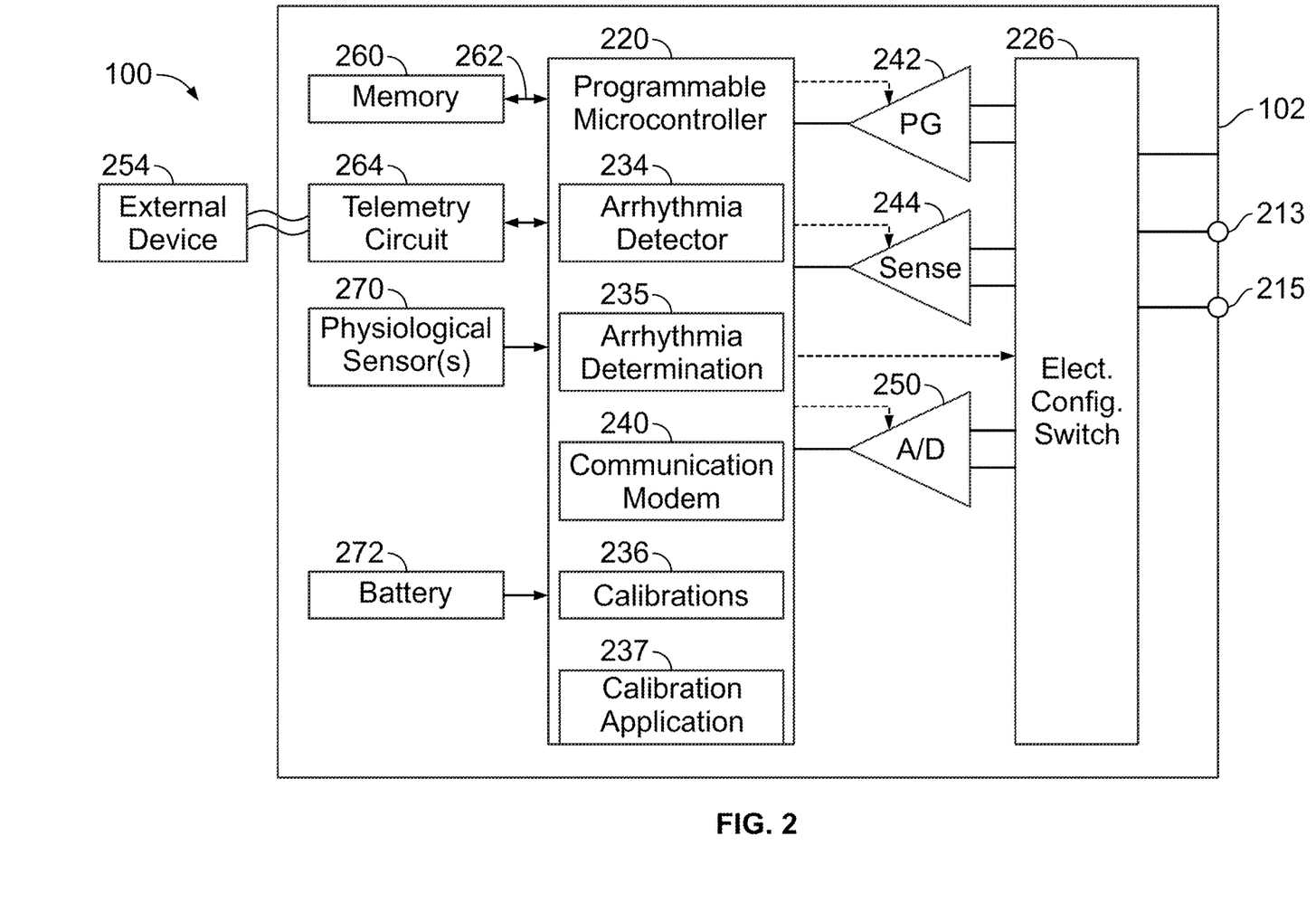
FIG. 2 illustrates a block diagram of an IMD formed in accordance with embodiments herein.

FIG. 2 shows an example block diagram of the IMD 100 formed in accordance with embodiments herein. In one example the IMD 100 can be a dual chamber pacemaker with unipolar leads. The IMD 100 may be implemented to monitor ventricular activity alone, or both ventricular and atrial activity through sensing circuitry. The IMD 100 has a housing 102 to hold the electronic/computing components. The housing 102 (which is often referred to as the "can," "case," "encasing," or "case electrode") may be programmably selected to act as an electrode, or case electrode, for certain sensing modes. Housing 102 further includes a connector (not shown) with at least one terminal 213 and optionally additional terminals 215. The terminals 213, 215 may be coupled to electrodes that are provided upon or immediately adjacent the housing 102. Optionally, more than two terminals 213, 215 may be provided in order to support more than two electrodes, such as for a bipolar sensing scheme that uses the housing 102, or case as a reference, case electrode. Additionally or alternatively, the terminals 213, 215 may be connected to one or more leads having one or more electrodes provided thereon, where the electrodes are located in various locations about the heart. The type and location of each electrode may vary.

The IMD 100 includes a programmable microcontroller 220 that controls various operations of the IMD 100, including cardiac monitoring. Microcontroller 220 includes a microprocessor (or equivalent control circuitry), RAM and/or ROM memory, logic and timing circuitry, state machine circuitry, and I/O circuitry. Microcontroller 220 may include an arrhythmia detector 234 and arrhythmia determination circuitry 235 that is configured to analyze the far field cardiac activity signals to identify the existence of an arrhythmia.

The IMD 100 further includes pulse generator (PG) circuitry 242 that generates stimulation pulses, or signals for delivery by one or more electrodes coupled thereto. In one example, the PG circuitry 242 is housed within the IMD, and in one example with the housing 102, or case. The PG circuitry 242 is controlled by the microcontroller 220 via a control signal. The PG circuitry 242 can be coupled to the select electrode(s) via an electrode configuration switch 226, which includes multiple switches for connecting the desired electrodes to the appropriate I/O circuits, thereby facilitating electrode programmability. The switch 226 can be controlled by a control signal from the microcontroller 220.

In one example, the PG circuitry 242 is configured to deliver a stimulus to the one or more of the electrodes. The stimulus can have a signal COI. In example embodiments, the signal COI can be an amplitude, frequency, pulse width, maximum amplitude, morphology, slope, energy level, or the like. In particular, the PG circuitry can provide a stimulus that generates a treatment, or therapy signal that results in therapy to the heart. In particular, in one example, the stimulus captures the heart because the energy level of the therapy signal results in a reaction, or pacing by the heart. To this end, the signal COI of the stimulus for the therapy signal is sufficient to stimulate a pace in the heart. Alternatively, the PG circuitry 242 may also provide a reduced stimulus that has an energy level that does not stimulate a pace in the heart (e.g. avoids capture), and instead provides a calibration signal that has a signal COI that does not stimulate a pace of the heart. However the signal COI of the calibration signal does allow measurement and analysis of the PG circuitry 242 and sensing circuitry 244.

Figure 3:
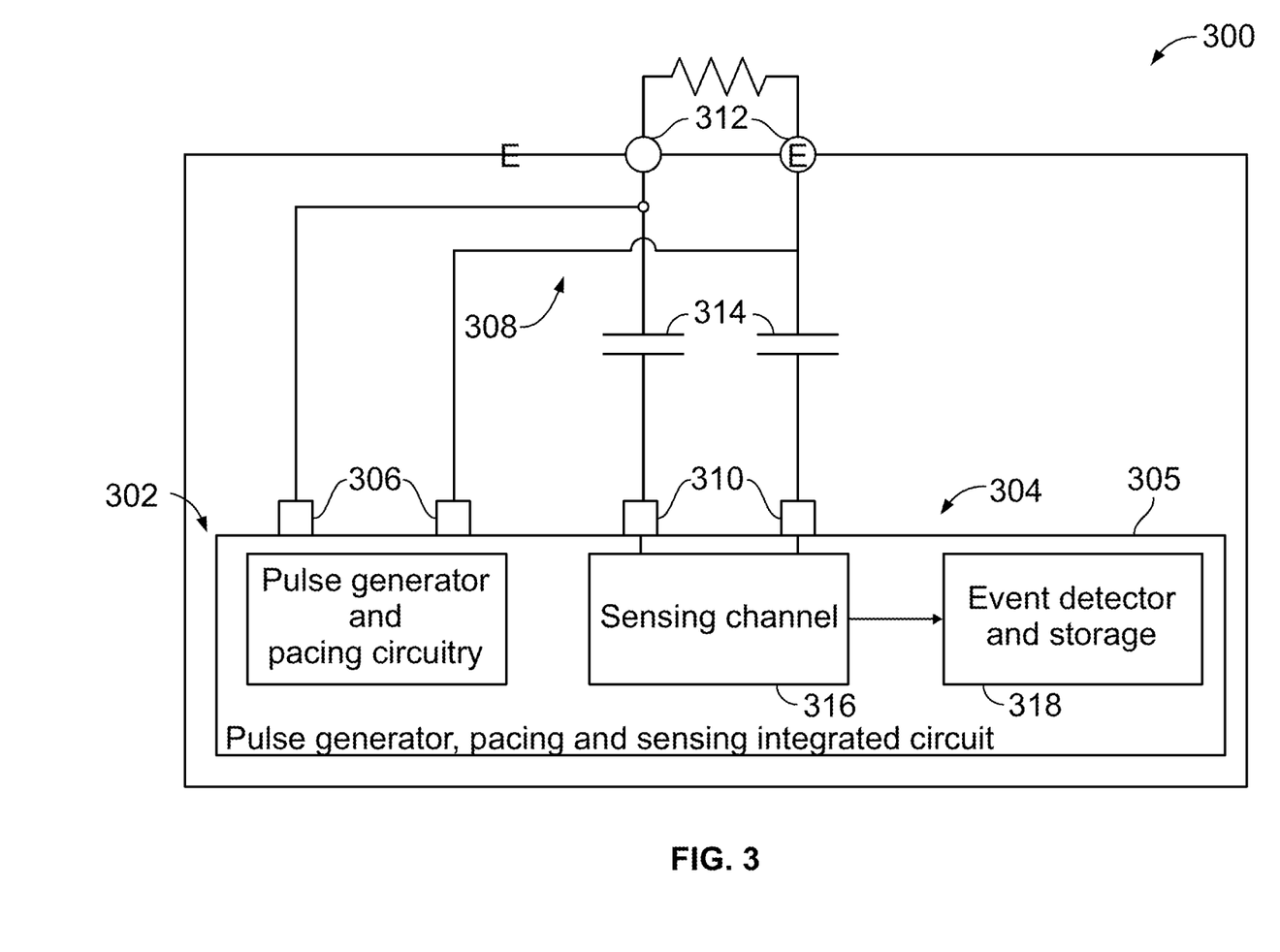
FIG. 3 illustrates a schematic diagram of a system for calibrating an IMD in accordance with embodiments herein.
Figure 4:
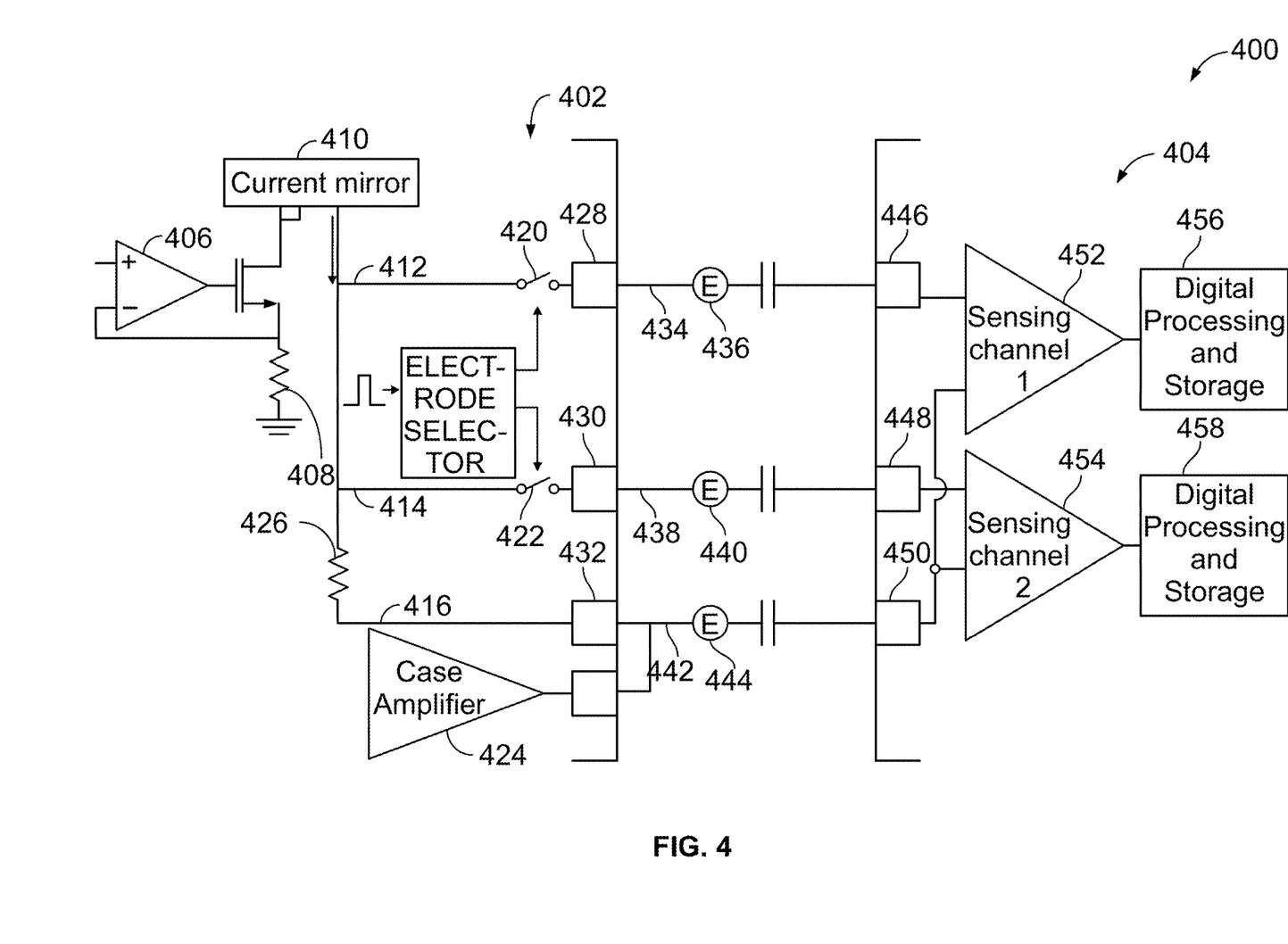
FIG. 4 illustrates a schematic diagram of a system for calibrating an IMD in accordance with embodiments herein.

The IMD 100 includes sensing circuitry 244 selectively coupled to one or more electrodes that perform sensing operations through one or more of the switches 226 to detect CA data indicative of cardiac activity. In one example, the sensing operations include collecting calibration signals through a sensing channel. The sensing circuitry 244 may include dedicated sense amplifiers, multiplexed amplifiers, or shared amplifiers. (FIGS. 3 and 4). It may further employ one or more low power, precision amplifiers with programmable gain and/or automatic gain control, bandpass filtering, and threshold detection circuit to selectively sense the COI. In one embodiment, switch 226 may be used to determine the sensing polarity of the CA signal by selectively closing the appropriate switches. The sensing circuitry 244 may also detect signal COI of signals or pulses generated by the PG circuitry, including amplitudes, pulse widths, and the like.

In one example, a single sensing circuitry 244 may be provided. Optionally, the IMD 100 may include multiple sensing circuits that comprise the sensing circuitry 244, where each sensing circuit is coupled to two or more electrodes and controlled by the microcontroller 220 to sense electrical activity detected at the corresponding two or more electrodes. The sensing circuitry 244 may operate in a unipolar sensing configuration or a bipolar sensing configuration. The output of the sensing circuitry 244 is connected to the microcontroller 220 which, in turn, determines when to store the CA data of the CA signals (digitized by an analog to digital converter (ADC) 250), calibration signals, etc. in the memory 260. The sensing circuitry can by utilized determine a measured impedance along a sensing vector between electrodes. Calibration of the sensing circuitry can therefore result in a calibration of the measured impedance along the sensing vector.

The sensing circuitry 244 is configured to define a sensing channel between one or more electrodes to sense signals indicative of a physiological activity of interest. Physiological activity may include heart beats, heart sounds, or the like. The signals may be generated as a result of a stimulus and may include therapy signals, calibration signals, atrial calibration signals, ventricular calibration signals, or the like. In one example, the sensing circuitry 244 is housed with the IMD. In an example, the sensing circuitry 244 is configured to collect a calibration signal over the sensing channel. In this manner, a signal COI of the calibration signal may be determined, and compared to a signal COI of a stimulus from the PG circuitry 242 resulting in the calibration signal. The analysis of the comparison allows one or more processors to determine and adjust a parameter of the sensing circuitry 244 or PG circuitry 242. In one example, the parameter is the gain of at least one amplifier of the PG circuitry 242 or sensing circuitry 244. Alternatively, the parameter may be the gain of more than one amplifier, a resistance value, a current value, a voltage value, a capacitance value, or the like. In another example, a sensitivity level may be a varied by adjusting a sensitivity correction factor parameter in the ADC 250. The ADC 250 converts the analog output of an amplifier to a digital value and applies the sensitivity correction factor to vary the digital value of the sensitive level. The adjustment may be made in real-time while the IMD is in use within a patient, accounting for changes to the PG circuitry 242 and sensing circuitry 244 during use. By providing the adjustment in real-time during use instead of prior to implanting the IMD, the sensing circuitry provides more accuracy during use.

In one example, the sensing circuitry 244 utilizes an automatic sensing adjustment based on a sensitivity or calibration profile 236. The calibration profile 236 is defined by calibration profile parameter settings and are indicative of the accuracy of the sensing circuitry. By calibrating the sensing circuitry 244 after the IMD has been implanted, and periodically in real-time while the IMD is in use, the sensing accuracy of the sensing circuitry is improved. To this end, the sensitivity of the sensing circuit 244 can be continuously adjusted by the microcontroller 220 in accordance with the calibration profile 236 during the life of the IMD.

The microcontroller 220 may also include a calibration application 237 the obtains the signal COI of the stimulus from the PG circuitry 242, and the signal CIO of a calibration signal from the sensing circuitry 244. The calibration application 237 can then be utilized to compare the signal CIO of the stimulus to the signal CIO of the calibration signal. The calibration application may also be utilized in association with a lookup table, decision tree, model, algorithm, artificial intelligence algorithm, formula, or the like to make determinations related to adjustments to a parameter of either the PG circuitry 242, the sensing circuitry 244, both, etc. Based on the determinations, adjustments to parameters can be made accordingly.

The IMD 100 further includes the ADC 250 coupled to one or more electrodes via a switch 226 to sample CA signals across any pair of desired electrodes. In addition, the ADC can sample therapy signals, calibration signals, atrial calibration signals, ventricular calibration signals, or the like, generated by the PG circuitry 242. In particular, the ADC 250 can digitize the analog output from the electrodes.

Although not shown, the microcontroller 220 may further include other dedicated circuitry and/or firmware/software components that assist in monitoring various conditions of the patient's heart and managing pacing therapies.

The IMD 100 is further equipped with a communication modem (modulator/demodulator) 240 to enable wireless communication. In one implementation, the communication modem 240 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 240 may be implemented in hardware as part of the microcontroller 220, or as software/firmware instructions programmed into and executed by the microcontroller 220. Alternatively, the modem 240 may reside separately from the microcontroller as a standalone component. The modem 240 facilitates data retrieval from a remote monitoring network. The modem 240 enables timely and accurate data transfer directly from the patient to an electronic device utilized by a physician. The modem 240 in one example is in communication with an external device 254 to provide COI of calibration signals, and adjustments to parameters of circuitry within the IMD 100. In this manner, if the same parameter in numerous different IMDs 100 must be adjusted, the information and data may be utilized to improve the IMD.

By way of example, the external device 254 may represent a bedside monitor installed in a patient's home and utilized to communicate with the IMD 100 while the patient is at home, in bed or asleep. The external device 254 may be a programmer used in the clinic to interrogate the IMD 100, retrieve data and program detection criteria and other features. The external device 254 may be a handheld device (e.g., smartphone, tablet device, laptop computer, smartwatch, and the like) that may be coupled over a network (e.g., the Internet) to a remote monitoring service, medical network and the like. The external device 254 may communicate with a telemetry circuit 264 of the IMD through a communication link 266. The external device 254 facilitates access by physicians to patient data as well as permitting the physician to review real-time CA signals, or real-time calibration signals and a signal COI of the calibration signal while collected by the IMD 100.

The microcontroller 220 is coupled to a memory 260 by a suitable data/address bus 262. The memory 260 stores the motion data, baseline motion data sets, CA signals, COI of calibration signals, calibrations signals, or the like associated with detection and determination of adjustments to the sensing circuitry 244, calibration circuitry 236, etc.

The IMD 100 may further include one or more physiologic sensors 270. For example, the physiologic sensor 270 may represent one or more accelerometers, such as a three-dimensional (3D) accelerometer. The sensor 270 may utilize a piezoelectric, a piezoresistive, and/or capacitive components are commonly used to convert the mechanical motion of the 3D accelerometer into an electrical signal received by the microcontroller 220. By way of example, the 3-D accelerometer may generate three electrical signals indicative of motion in three corresponding directions, namely X, Y and Z directions. The electrical signals associated with each of the three directional components may be divided into different frequency components to obtain different types of information therefrom.

The physiologic sensor 270 collects device location information with respect to gravitational force while the IMD 100 collects CA signals in connection with multiple cardiac beats. The microcontroller 220 may utilize the signals from the physiologic sensor 270 in the manner described in U.S. Pat. No. 6,937,900, titled "AC/DC Multi-Axis Accelerometer for Determining A Patient Activity and Body Position," the complete subject matter which is expressly incorporated herein by reference. While shown as being included within the housing 102, the physiologic sensor(s) 270 may be external to the housing 102, yet still, be implanted within or carried by the patient.

The physiologic sensor 270 may be further configured to obtain motion data in the form of acceleration signatures generated during cardiac beats. The acceleration signatures from the sensor 270 are provided to the microcontroller 220 and are analyzed. The motion data is indicative of one or more of the patient posture or the respiration cycle.

The IMD can also include a battery 272 for operation. The microcontroller 220 can determine the use of any of the components of the IMD, including the calibration application 237 to ensure that calibration of circuitry of the IMD does not drain or significantly decrease the life of the battery, offsetting advantages realized from the calibration in real-time while the IMD is implanted in a patient.

FIG. 3 illustrates a schematic diagram of therapy circuitry 300 of an IMD for providing therapy to a patient. The therapy circuitry 300 is located within a housing of an IMD. The therapy circuitry 300 includes pulse generator (PG) circuitry 302 and sensing circuitry 304. The therapy circuitry can be configured to provide calibration of the PG circuitry 302 and sensing circuitry 304 when the IMD is implanted in a patient. To this end, calibration of the therapy circuitry may occur periodically after implant to ensure and improve accuracy of the therapy of the IMD. In one example, the PG circuitry 302 and sensing circuitry coupled to board, circuit board, printed circuit board, substrate, etc. providing an integrated circuit 305. Alternatively, the PG circuitry 302 and sensing circuitry 304 are not provided on a similar substrate.

PG conductors 306 can be coupled to the PG circuitry 302 and be disposed between the PG circuitry 302 and the header nodes 308 internal to the housing the IMD. In one example, the PG conductors 306 are pacing pads, where the example embodiment of FIG. 3 illustrates a first pacing pad and a second pacing pad. To this end, the PG conductors 306 provide a stimulus to the header nodes 308 to be detected by the sensing circuitry 304.

The stimulus results in the generation of a signal that has known signal characteristics of interest (COI). In one example, the stimulus is an atrial stimulus, while in another example, the stimulus is a ventricular stimulus. Signal COI can include amplitude, pulse width, frequency, energy level, or the like. Because the PG circuitry 302 provides a known stimulus, the signal COI of the signal generated by the PG circuitry 302 is also known. In one example, the PG conductors 306 provide a stimulus that results in a therapy signal being generated that includes an energy level to provide therapy to the heart. In one example, the therapy can be a pace. Alternatively, the PG conductors 306 can provide a stimulus that results in a calibration signal being generated that includes an energy level that is insufficient to provide therapy to the heart. In particular, the stimulus has an energy level that avoids capture, or undesired therapy to the heart. To this end, the stimulus that generates the therapy signal has a greater energy level than the stimulus that generates the calibration signal. In example embodiments, the energy level may be measured as, or be related to any one of voltage, current, amplitude, longer pulse width, or the like. Still, regardless of if a therapy signal, calibration signal, atrial calibration signal, ventricular calibration signals, or other signal are generated by the stimulus, the signal COI of the signal generated by the PG circuitry 302 is known.

The header nodes 308 are disposed between the PG conductors 306 and sensing conductors 310. In one example, the sensing conductors 310 are sensing pads. In another example, each sensing pad is a sensing channel integrated circuit (IC) pad.

Within each header node 308 is an electrode 312 that receives the stimulus from the PG circuitry 302. The electrodes 312 function in the IMD to sense physiological activity of interest, including heart beats, heart signals, heart sounds, or the like. The electrodes 312 may be ring electrodes, atrial ring (Aring) electrodes, ventricle ring (Vring) electrodes, case electrodes, ring electrodes, tip electrodes, positive electrodes, negative electrodes, or the like. In one example, a measured impedance may be provided along a sensing vector between any two electrodes 312. The PG conductors 306 are utilized to apply the stimulus, or internally generated pulse, to the electrodes 312, and the sensing conductors 310 are utilized to obtain a signal from the electrodes 312 for utilization by sensing circuitry 304. In one example, capacitors 314 may also be utilized for protection of the therapy circuitry 300. In one embodiment, the capacitors 314 may be shunt capacitors.

The sensing circuitry 304 can be configured to collect a signal that is generated from the stimulus from the PG circuitry, whether a calibration signal, therapy signal, atrial calibration signal, ventricular calibration signal, etc. as an input. In particular, the signal at the electrodes 312 can be utilized for evaluating the signal through a sensing channel 316 by analyzing the signal COI of the signal once received by the sensing circuitry 304. Once the signal reaches the sensing channel 316, a detector and storage device 318 may be utilized for detecting the signal, including calibration signals, therapy signals, etc. for storage and processing. In particular, when a calibration signal is generated, the signal COI of the stimulus generated by the PG circuitry can be compared the signal COI of the calibration signal received by the sensing circuitry. The detector and storage device 318 can then be utilized to for processing, and if the COI of the stimulus and the COI of the calibration signal do not match, adjustment to a parameter of the PG circuitry or the sensing circuitry can be made. In one example, the gain of one or more amplifiers of the PG circuitry or sensing circuitry may be adjusted. Alternatively, a sensitivity level may be varied by adjusting a sensitivity correction factor in an analog to digital converter (ADC) of the sensing circuitry may be adjusted. In one example, the ADC can convert an analog output of an amplifier to a digital value, and obtain a sensitivity correction factor to vary the digital value (e.g. 0-1000). In this manner, the sensitivity correction factor is a parameter that can be adjusted to vary the sensitivity level of the sensing circuitry 304.

In all, when generating a calibration signal, signal COI such as pulse amplitude of the calibration signal are known based on the stimulus from the PG circuitry 302. Therefore, accurate sensitivity is obtained at the output of the sensing channel 316. The stimulus can then be repeated to provide calibration signals at any sensing channel setting, in order to calibrate the different electrical components of the IMD. Because the calibration signal is applied at the first and second electrode 304, 306, the same as a therapy signal, no comparison error exists. Thus, the path of the calibration signal to the sensing channel output includes all external and internal components to the IC that define the sensing channel gain and bandwidth characteristics, or sensitivity for a therapy signal. Consequently, an accurate, and continuously reproducible calibration of the sensing circuitry can be accomplished.

FIG. 4 illustrates a schematic diagram of another example embodiment of therapy circuitry 400 for an IMD. In one example, the IMD can be a dual chamber pacemaker with unipolar leads. Similar to the example embodiment of FIG. 3, the therapy circuitry 400 includes PG circuitry 402 that provides a stimulus for generating a signal, and sensing circuitry 404 for collecting the signal. In one example, the stimulus is an atrial stimulus, while in another example, the stimulus is a ventricular stimulus. Based on the energy level of the stimulus a therapy signal, calibration signal, atrial calibration signal, ventricular calibration signal, other signal, etc., may be generated by the PG circuitry 402.

The PG circuitry 402 can include a first amplifier 406. The first amplifier 406 functions to provide a buffer (e.g. to avoid loading the VREF output) to apply VREF voltage to the control element 408 to generate the signal. In one example the control element 408 is a first resistor. The signal is then passed to a current mirror 410 the generates a signal with known signal COI. In this example, a signal transmits through three parallel signal channels 412, 414, 416. An electrode controller 418 actuates a first switch 420 and second switch 422 to determine whether the signal transmits through the first signal channel 412, or the second signal channel 414. In one example, the electrode controller includes a timing element that can control the pulse width of the signal utilizing the first switch 420 and/or second switch 422. When the first switch 420 is closed, the second switch 422 is open, and the signal travels through the first signal channel 412. Alternatively, when the second switch 422 is closed, the first switch 420 is open, and the signal travels through the second signal channel 414. Meanwhile, in parallel to both the first signal channel 412 and the second signal channel 414, a third signal channel 416 is provided that includes a second amplifier 424. In one example, the second amplifier 424 is a case amplifier. The second amplifier 424 is coupled to a second control element 426, that in one example is a resistor. The second control element can convert the current to voltage. In one example, the second amplifier 424 drives a case node (e.g. third header node 442). Each of the first and second amplifiers 406, 424, their corresponding control elements 408, 426, the current mirror 410, and electrode controller 418 at least partially comprise the PG circuitry 402.

The first signal channel 412 also includes a first PG conductor 428, the second signal channel 414 includes a second PG conductor 430, and the third signal channel 416 includes a third PG conductor 432. The first PG conductor 428 provides stimulus for a signal through a first header node 434 to a first electrode 436 when the first switch 420 is closed. In one example, the signal may be a therapy signal, while alternatively the signal may be a calibration signal. In yet another example, the first electrode may be an atrial ring electrode, and the signal may be an atrial calibration signal. The second PG conductor 430 provides stimulus for a signal through a second header node 438 to a second electrode 440 when the second switch 422 is closed. In this manner, the switches 420 and 422 are configured to connect and disconnect the PG circuit 402 to the header nodes 434, 438. In one example, the second electrode can be a ventricle ring electrode, and the signal a ventricular calibration signal. Meanwhile, the third PG conductor 432 provides stimulus for a signal through a third header node 442 to a third electrode 444. In one example, the third electrode can be a case electrode. In another example a first measured impedance can be detected along a sensing vector between the first electrode 436 and third electrode 444, while a second measured impedance can be provided along a sensing vector between the second electrode 440 and the third electrode 444. Within each header node, a capacitor can be provided for additional protection. In one example, each capacitor is a shunt capacitor.

The first electrode 436 provides an input to a first sensing conductor 446. In one example, the first sensing conductor is a first sensing IC pad. The second electrode 440 provides an input to a second sensing conductor 448, while the third electrode 444 provides an input to a third sensing conductor 450. In one example, the second sensing conductor 448 is a second sensing IC pad, while the third sensing conductor 450 is a third sensing IC pad. Each of the first, second, and third sensing conductors 446, 448, 450 provide parallel paths to the sensing circuitry 404.

The sensing circuitry 404 includes a first sensing channel 452 and second sensing channel 454. In particular, the sensing circuitry 404 is configured to collect signals, including calibration signals over the sensing channels 452, 454. When the first switch 420 is closed, the first sensing channel 452 includes inputs from the first sensing conductor 446 and the third sensing conductor 450. In one example, when the first electrode 436 is an atrial ring electrode and the third electrode 444 is a case electrode, the case electrode may function as a ground, and the first sensing channel 452 functions as an atrial sensing channel. When the second switch 422 is closed, the second sensing channel 454 includes inputs from the second sensing conductor 448 and the third sensing conductor 450. In an example, when the second electrode 440 is a ventricle ring electrode and the third electrode 444 is a case electrode, the case electrode may function as a ground, and the second sensing channel 454 functioning as a ventricle channel.

In one example, the IMD may be biased with respect to the IMD ground from the second amplifier 424 through the third electrode 444, that can be a case electrode. In the example, when the first electrode 436 is an Aring electrode, the second electrode 440 is a Vring electrode, and the third electrode 444 is a case electrode, when a pulse, or signal, is generated between either Aring electrode and case electrode or Vring electrode and case electrode, these are input into the first sensed channel 452 and second sensed channel 454, respectfully. The pulse amplitude is generated using a current flowing through a control element 408, 426, or resistor such that:

$$V_{pulse} = R2 * I_{pulse}$$

And:

$$I_{pulse} = \frac{V_{REF}}{R1}$$

Then $V_{pulse}$ can be written as:

$$V_{pulse} = \frac{V_{REF} R2}{R1}$$

R1 (e.g. first control element 408) and R2 (e.g. second control element 426) are programmable thus giving flexibility to pulse amplitude. The pulse duration is defined by the input pulse controller circuit. Pulse duration is also programmable such as to adapt the pulse width to the sensing channel bandwidth that is selected. Furthermore, the electrode controller 418 can send the pulse to either set of electrodes. In this manner, the gain may be a parameter that is adjusted to vary the signal sensing by the sensing circuitry. In example embodiments, the parameter may be adjusted to vary the signal to correct an error, provide more precise sensing of individual signals that are being sensed, or the like.

The first sensing channel 452 may be coupled to a first digital processing and storage device 456. The first digital processing and storage device may include a first analog to digital converter (ADC) and a first registry, memory, communication path to a memory, or the like. Meanwhile, the second sensing channel 454 can be coupled to a second digital processing and storage device 458. Similarly, the second digital processing and storage device 458 can include a second ADC, registry, memory, communication to memory, etc. Each ADC may include a sensitivity correction factor associated with a sensitivity level of the sensing circuitry 404. In one example, the sensitivity correction factor may be parameter that is adjusted to correct the analog output of an amplifier to a digital value. For example, an ADC can convert an analog output of an amplifier to a digital value (e.g. 0-1000). A correction factor may be stored in a register to correct the digital value output to provide an accurate sensitivity level. (e.g. if the ADC outputs a value of 400, the correction factor may adjust it to 380, whereas alternatively the correction factor could adjust it to 420). By adjusting the parameter of the correction factor, the sensing circuitry 404 may be corrected to match the signal COI of a calibration signal to a signal COI of a stimulus.

In this manner, a built-in test circuit related to the operation of the sensing circuit 404 for real-time calibration is provided. Because the sensing circuit 404 is built-in, proper protection for enabling this sensing circuit 404 can be controlled. For example, a two-step process to enable the protection feature, like writing a special value to a register to unlock the enable, and then write another value to a different register to perform the calibration. In one example, the two writes are to be completed within a certain time limit for further protection. Therefore, improved calibration is realized.

Figure 5:
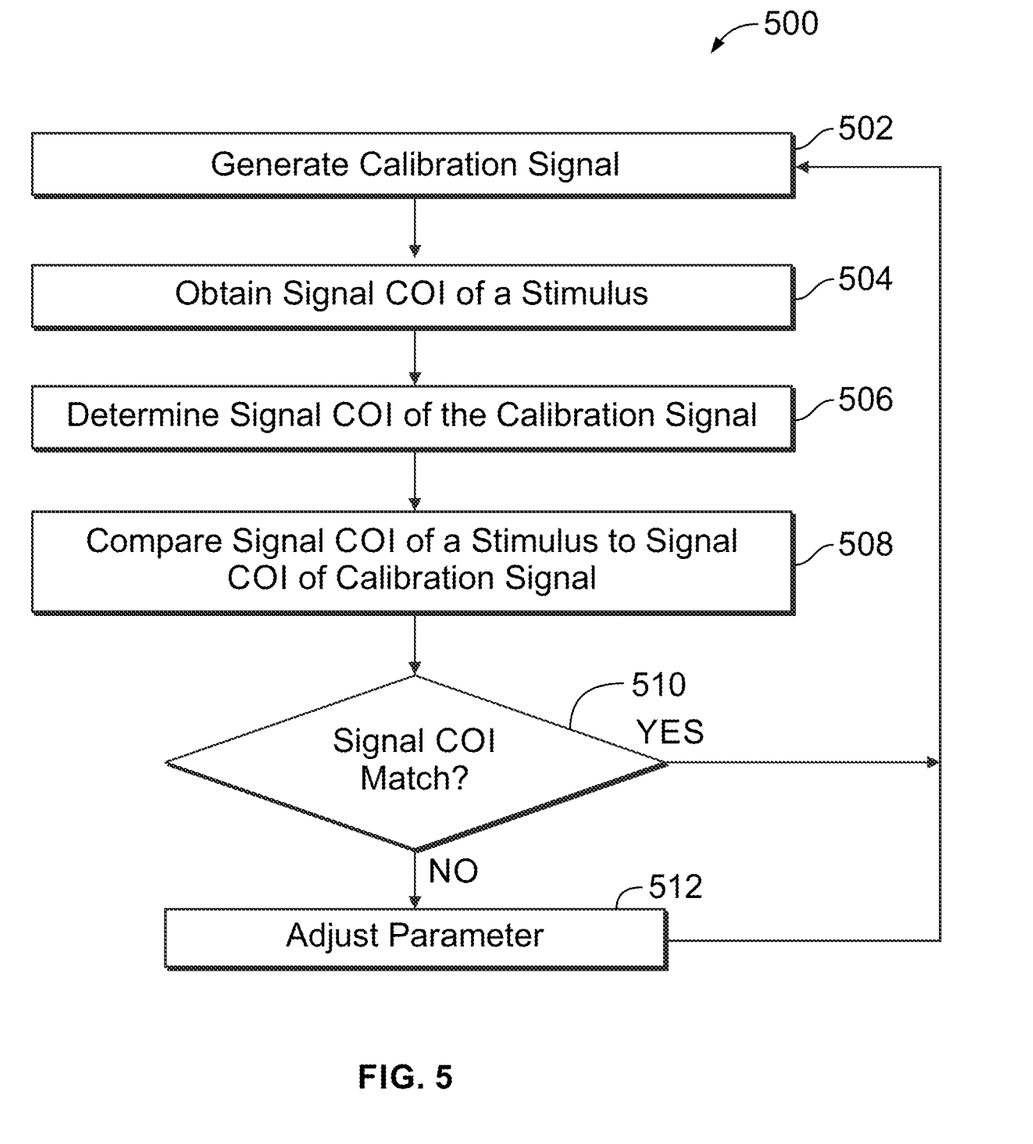
FIG. 5 is a flow block diagram of a method for calibrating an IMD in accordance with embodiments herein.

FIG. 5 illustrates a block flow diagram of a process 500 for calibrating an IMD. In one example, the IMD is the IMD illustrated in any of the previous Figures, and the process may be implemented by any of the circuits or components illustrated in the previous figures. In one example, the IMD is a pacemaker that includes at least three electrodes, including an atrial ring electrode, ventricle ring electrode, and case electrode.

At 502, one or more processors generate a calibration signal. In one example, PG circuitry is provided that provides a stimulus for generating the calibration signal that is received by one or more electrodes of the IMD. In an example, the PG circuitry can vary its output to output a stimulus that is able to pace the heart via the electrodes, and output a stimulus that is insufficient to pace the heart via the electrodes and instead outputs a calibration signal for calibrating the IMD. When the output signal is a calibration signal that is not able to stimulate the heart, the stimulus has an energy level that avoids capture. In addition, the calibration signal includes an energy level that is less than a therapy signal generated by the PG circuitry.

At 504, the one or more processors, obtains a signal COI of a stimulus delivered to one or more electrodes of a system. In one example, the stimulus is delivered by PG circuitry to generate a signal, or pulse, at the electrodes. In one example, the stimulus is an atrial stimulus, while in another example, the stimulus is a ventricular stimulus. In one example, the signal may be a therapy signal resulting in therapy provided to the heart of a patient, such as a pace. In another example, the signal can be a calibration signal that avoids capture by the heart such that the heart does not receive a pace or other unintended therapy. Instead, the calibration signal is provided only for calibrating the IMD, and not for therapeutic purposes. In one example, the calibration signal has known signal COI. The signal COI may include the calibration signal amplitude, maximum amplitude, minimum amplitude, wavelength, pulse width, frequency, energy level, or the like. The signal COI of the stimulus may be communicated to a register, memory, or the like for use by the one or more processors in determining calibration of the IMD.

At 506, the one or more processors determine a signal COI of the calibration signal from sensing circuitry. Again, a signal COI can include amplitude, maximum amplitude, minimum amplitude, wavelength, pulse width, frequency, or the like. In one example, sensing circuitry determines the signal COI of the calibration signal generated by the PG circuitry. In example embodiments, the sensing circuitry may include plural sensing channels that receive the calibration signal. In some embodiments, a first sensing channel may receive a first calibration signal, and then a second sensing channel may receive a later second calibration signal. In particular, in one example, the PG circuitry may include a switch that directs the stimulus to a desired channel. In this manner, each electrode of an IMD can receive a calibration signal, allowing calibration of each individual electrode of the system.

At 508, the one or more processors compare the signal COI of the stimulus to the signal COI of the calibration signal. Because the signal COI of the stimulus provided by the PG circuitry is known, the signal COI of the calibration signal determined by the sensing circuitry should match. If the signal COI of the stimulus does not match the signal COI of the calibration signal, then adjustment of a parameter of the PG circuitry or sensing circuitry is required.

At 510, a determination is made whether the signal COI of the stimulus matches the signal COI of the calibration signal. If the signal COI of the stimulus matches the signal COI of the calibration signal, then no adjustment of a parameter is made, and the one or more processors continue periodically generating the calibration signals to verify the sensing circuitry continues accurately sensing the stimulus from the PG circuitry. In one example, the calibration signal is a first calibration signal received by a first electrode, and a second calibration signal is input to a second electrode. Alternatively, the same electrode may periodically receive a new calibration signal, to repeatedly calibrate the IMD as needed.

If at 510, a determination is made that the signal COI of the stimulus does not match the signal COI of the calibration signal, then at 512, one or more processors adjust a parameter of the PG circuitry or sensing circuitry based on the comparison. The adjustment occurs in real-time, avoiding the need to adjust or perform complex testing prior to implant. In examples, the parameter can be the gain, a sensitivity correction factor in an ADC, resistor setting, or the like. In one example, an ADC converts the analog output of an amp to a digital value (e.g. 0-1000), and then a sensitivity correction factor is utilized to vary increase or decrease the digital value to provide an accurate sensitivity level. To this end, the parameter may be increased, decreased, enhanced, multiplied, or the like based on the COI of the calibration signal. In particular, a lookup table, decision tree, mathematical formula, mathematical model, mathematical formula, artificial intelligence algorithm, or the like may be utilized to determine the adjustment of a parameter based on the signal COI of the calibration signal.

After the adjustment of the parameter, the one or more processors continue to generate calibration signals with the PG circuitry for detection by the sensing circuitry. In particular, the one or more processors select adjustment of the parameter in one of the atrial sensing channel, or the ventricular sensing channel to update calibration to ensure the adjustment of the parameter accurately varied the sensing circuitry. Then, after the calibration is updated from the adjustment of the parameter, additional subsequent calibration signals can be provided. Consequently, calibration is able to occur after an IMD in implanted, and the IMD can be repeatedly verified and calibrated. The frequency of use of the calibration signal may be varied to reduce battery use. To this end, if calibration is required, the one or more processors may increase the frequency until the IMD is providing accurate results. In all, enhanced accuracy of the sensing circuitry is provided.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Embodiments may be implemented utilizing all or portions of the methods and systems described in U.S. application Ser. No. 16/930,791, filed Jul. 16, 2020 and titled "METHODS, DEVICES AND SYSTEMS FOR HOLISTIC INTEGRATED HEALTHCARE PATIENT MANAGEMENT".

The physiologic sensor may be implemented as an accelerometer and may be implemented utilizing all or portions of the structural and/or functional aspects of the methods and systems described in U.S. Pat. No. 6,937,900, titled "AC/DC Multi-Axis Accelerometer for Determining A Patient Activity and Body Position;" U.S. application Ser. No. 17/192, 961, filed Mar. 5, 2021, titled "SYSTEM FOR VERIFYING A PATHOLOGIC EPISODE USING AN ACCELEROMETER"; U.S. application Ser. No. 16/869,733, filed May 8, 2020, titled "METHOD AND DEVICE FOR DETECTING RESPIRATION ANOMALY FROM LOW FREQUENCY COMPONENT OF ELECTRICAL CARDIAC ACTIVITY SIGNALS;" U.S. application Ser. No. 17/194,354, filed Mar. 8, 2021, titled "METHOD AND SYSTEMS FOR HEART CONDITION DETECTION USING AN ACCELEROMETER," the complete subject matter which is expressly incorporated herein by reference.

All references, including publications, patent applications and patents, cited herein are hereby incorporated by reference to the same extent as if each reference were individually and specifically indicated to be incorporated by reference and were set forth in its entirety herein.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices, and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system, comprising:
electrodes configured to be implanted in a body;
pulse generator (PG) circuitry to deliver a stimulus to one or more of the electrodes, the stimulus having a signal characteristic of interest (COI);
sensing circuitry configured to define a sensing channel between one or more of the electrodes to sense signals indicative of a physiologic activity of interest, the sensing circuitry further configured to collect a calibration signal over the sensing channel;
wherein the sensing circuitry and PG circuitry are housed within an implantable medical device (IMD);
one or more processors; and a memory coupled to the one or more processors, the memory configured to store program instructions that are executable by the one or more processors to:
determine a signal COI of the calibration signal;
compare the signal COI of the stimulus to the signal COI of the calibration signal; and
adjust a parameter of the sensing circuitry or PG circuitry based on the comparison.

2. The system of claim 1, wherein the one or more processors are further configured to adjust, as the parameter, at least one of a gain, or a sensitivity correction factor in an analog/digital converter (ADC), of the sensing circuitry.

3. The system of claim 1, wherein to adjust the parameter of the sensing circuitry or PG circuitry based on the comparison, the one or more processors are further configured to convert, with analog to digital converter (ADC) of the sensing circuitry, an analog output of an amplifier to a digital value; and obtain a sensitivity correction factor to vary the digital value.

4. The system of claim 1, wherein the sensing circuitry includes a first header node and a second header node coupled to a first analog to digital converter, and a third header node coupled to a second analog to digital converter.

5. The system of claim 1, wherein the PG circuitry includes a first amplifier electrically coupled to a first control element, and second amplifier electrically coupled to a second control element.

6. The system of claim 5, further comprising switches configured to connect and disconnect the PG circuit to the header nodes.

7. The system of claim 1, further comprising:
sensing conductors, within the sensing channel, extending between the sensing circuitry and corresponding header nodes internal to a housing of the IMD; and
PG conductors extending between the PG circuitry and the header nodes internal to the housing of the IMD.

8. The system of claim 1, wherein the stimulus has an energy level that avoids capture.

9. The system of claim 1, wherein the sensing channel utilizes a first electrode and a second electrode from the electrodes and the stimulus is delivered to the first electrode and a third electrode from the electrodes.

10. The system of claim 9, wherein the sensing channel includes an atrial sensing channel between the first electrode and the third electrode and a ventricular sensing channel between the second electrode and the third electrode.

11. The system of claim 10, wherein the PG circuitry is configured to deliver an atrial calibration stimulus to the first electrode and third electrode and to deliver a ventricular calibration stimulus to the second electrode and third electrode.

12. The system of claim 10, wherein the one or more processors are further configured to select adjustment of the parameter in one of the atrial sensing channel, or the ventricular sensing channel to update calibration.

13. The system of claim 1, wherein the stimulus is one of a therapy stimulus or a calibration stimulus.

14. The system of claim 13, wherein the therapy stimulus provides a greater energy level than an energy level of the calibration stimulus.

15. A method for calibrating sensing circuitry of an implantable medical device, the method comprising:
delivering, with pulse generator (PG) circuitry, a stimulus to one or more electrodes configured to be implanted in a body, the stimulus having a signal characteristic of interest (COI);
sensing, with the sensing circuitry, signals indicative of physiologic activity of interest, wherein the sensing circuitry and PG circuitry are housed within the implantable medical device (IMD);
collecting, with the sensing circuitry, a calibration signal over a sensing channel;
determining a signal COI of the calibration signal;
comparing the signal COI of the stimulus to the signal COI of the calibration signal; and
adjusting a parameter of the sensing circuitry or PG circuitry based on the comparison.

16. The method of claim 15, wherein adjusting the parameter of the sensing circuitry or PG circuitry includes at least one of adjusting a gain of the PG circuitry, or adjusting a sensitivity correction factor in an analog to digital converter (ADC) of the sensing circuitry.

17. The method of claim 15, wherein adjusting the parameter of the sensing circuitry or PG circuitry comprises:
converting, with an analog to digital converter (ADC) of the sensing circuitry, an analog output of an amplifier to a digital value; and
obtaining a sensitivity correction factor to vary the digital value.

18. The method of claim 15, further comprising delivering an atrial calibration stimulus to a first electrode and a third electrode of the sensing circuitry to generate an atrial calibration signal, and delivering a ventricular calibration stimulus to a second electrode and the third electrode to generate a ventricular calibration signal.

19. The method of claim 18, further comprising actuating, with an electrode controller, a first switch to deliver the atrial calibration stimulus to the first electrode and the third electrode, and a second switch to deliver the ventricular calibration signal to the second electrode and the third electrode.

20. The method of claim 15, further comprising:
selecting adjustment of the parameter in one of an atrial sensing channel, or a ventricular sensing channel; and
calibrating the sensing circuitry based on the adjustment selected.

* * * * *